United States Patent [19]

Mattern

[11] 4,052,406
[45] Oct. 4, 1977

[54] PROCESS FOR THE PRODUCTION OF 3-HYDROXY-2-IMINO-(2H)-PYRIDINESULPHONIC ACID MONOHYDRATE

[75] Inventor: Günter Mattern, Liestal, Switzerland

[73] Assignee: Ciba-Geigy Corporation, Ardsley, N.Y.

[21] Appl. No.: 690,497

[22] Filed: May 27, 1976

[51] Int. Cl.$^2$ ............................................. C07D 213/73
[52] U.S. Cl. ...................... 260/294.8 R; 260/294.8 C; 260/294.8 F
[58] Field of Search ................................ 260/294.8 R

[56] References Cited

U.S. PATENT DOCUMENTS

| 3,663,555 | 5/1972 | Petersen et al. | 260/294.8 R |
| 3,706,753 | 12/1972 | Petersen et al. | 260/294.8 R |
| 3,808,218 | 4/1974 | Kristinsson et al. | 260/294.8 K |

Primary Examiner—Alan L. Rotman
Attorney, Agent, or Firm—Karl F. Jorda

[57] ABSTRACT

A process for the production of 3-hydroxy-2-imino-1(2H)-pyridinesulphonic acid comprising oxidation of furfurol and reaction of the oxidation product with sulphamic acid is disclosed which is carried out in the presence of an oxyacid of tri- or pentavalent phosphorus.

8 Claims, No Drawings

PROCESS FOR THE PRODUCTION OF 3-HYDROXY-2-IMINO-(2H)-PYRIDINESULPHONIC ACID MONOHYDRATE

The present invention relates to a process for the production of 3-hydroxy-2-imino-1(2H)-pyridinesulphonic acid monohydrate by oxidation of furfurol and reaction of the oxidation product with sulphamic acid.

3-Hydroxy-2-imino-1(2H)-pyridinesulphonic acid monohydrate is a valuable intermediate for the production of pesticidal active substances. Such active substances are described, for example, in the U.S. Pat. No. 3,808,218. They are obtained as follows using 3-hydroxy-2-imino-1(2H)-pyridinesulphonic acid monohydrate as the starting material:

3-hydroxy-2-imino-1(2H)-pyridinesulphonic acid monohydrate is firstly thermally decomposed, by the method described in the U.S. Pat. No. 3,706,753, to give 2-amino-3-hydroxy-pyridine; when subsequently reacted with this, phosgene and thiophosgene yield oxazolo[4,5-b]pyridin-2[3H]-one and oxazolo[4,5-b]pyridine-2(3H)-thione, respectively. Either of these is then converted, by chlorination, bromination or nitration, into an oxozolo [4,5-b]pyridine derivative of the formula

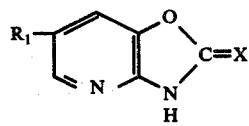

wherein
R₁ represents chlorine, bromine or the nitro group, and
X represents oxygen or sulphur,
which can then be reacted further, by the methods described in the U.S. Pat. No. 3,808,218, to yield pesticidally effective thiophosphoric acid derivatives and thiophosphonic acid derivatives.

From the U.S. Pat. No. 3,663,555, there is known a process for producing 3-hydroxy-2-imino-1(2H)-pyridinesulphonic acid monohydrate, which process comprises firstly reacting chlorine or a compound releasing chlorine in an aqueous medium, with a pH value of below 6, with furfurol, whereby the molar ratio of furfurol to chlorine, or to the compound releasing chlorine, is between 1:1 and 2:3; adding to the reaction mixture a solution of sulphamic acid; adjusting the pH value of the mixture, at the latest immediately after the addition of the sulphamic acid, by the addition of alkali to a value of between 0.5 and 6; and separating the formed 3-hydroxy-2-imino-1(2H)-pyridinesulphonic acid monohydrate from the reaction mixture. This process is however unsatisfactory for commercial manufacture of 3-hydroxy-2-imino-1(2H)-pyridinesulphonic acid monohydrate, since the yield obtained is only about 30% of theory, relative to furfurol.

The subject of the present invention is therefore a process by which 3-hydroxy-2-imino-1(2H)-pyridine-sulphonic acid monohydrate can be produced in a satisfactory yield.

It has been found that the monohydrate of 3-hydroxy-2-imino-1(2H)-pyridinesulphonic acid can be produced in good yields starting with furfurol by a process wherein furfurol is oxidised in an aqueous medium at a temperature of −10° to 0°C, with a pH value of 0 to 0.5, in the presence of an oxyacid of tri- or pentavalent phosphorus; the oxidation product is subsequently reacted with 2 to 3 moles of sulphamic acid per mole of employed furfurol; and the formed 3-hydroxy-2-imino-1(2H)-pyridinesulphonic acid-monohydrate is separated. Suitable oxyacids of tri- or pentavalent phosphorus are phosphoric acid, pyrophosphoric acid, metaphosphoric acid, phosphorous acid, as well as water-soluble phosphonic acids, especially methanephosphonic acid and ethanephosphonic acid. Among the aforementioned oxyacids of tri- and pentavalent phosphorus, phosphoric acid and phosphorus acid are preferred. The oxyacids of tri- and pentavalent phosphorus are used in amounts of 0.4 to 4 moles, preferably about 1 mole, per mole of employed furfurol. It is also possible to use, instead of the free acids, the water-soluble salts thereof, particularly alkali salts or ammonium salts.

The pH-value of the reaction mixture of 0 to 0.4 can be obtained by the addition of one of the aforementioned oxyacids of tri- or pentavalent phosphorus, or by the addition of a mixture of one of these acids with hydrochloric acid.

Oxidising agents that can be used are chlorine, substances releasing chlorine, such as alkali hypochlorite, bromine, sodium bromate, potassium bromate or chlorine in the presence of hydrogen bromide. Particularly suitable oxidising agents are bromine and sodium bromate and potassium bromate. It is advantageous to add, before commencement of oxidation, an alkali chloride or alkaline-earth chloride or an alkali bromide or alkaline-earth bromide in amounts of 0.01 to 1 mole per mole of employed furfurol. The use of an alkaline-earth chloride or alkali chloride is recommended, especially with the employment of sodium bromate or potassium bromate or of bromine as the oxidising agent.

A preferred embodiment of the process according to the invention comprises the oxidation of furfurol in an aqueous medium in the presence of 1 mole of phosphoric acid or phosphorus acid and 0.1 − 0.3 mole of an alkali chloride or alkaline-earth chloride or of an alkali bromide or alkaline-earth bromide with about the stiochiometric amount of sodium bromate or potassium bromate at −8° to −2° C, with a pH value of 0 to 0.3; the addition to the reaction mixture immediately afterwards, at −5° to 0° C, of a solution, adjusted to pH 1 to 2, of 3 moles of sulphamic acid per mole of employed furfurol; and the complete reaction of the mixture at 5° to 25° C.

It becomes possible with the process of the invention to increase the yield of 3-hydroxy-2-imino-1(2H)-pyridine-sulphonic acid monohydrate compared with the yield obtained using the known mode of procedure. Depending on the employed oxyacid of tri- or pentavalent phosphorus and on the oxidising agent used, there are obtained yields of between 47 and 60% of theory. The carrying out of the process with sodium bromate or potassium bromate as the oxidising agent offers the additional advantage of a lower salt contamination of the waste-water.

The process of the invention is further illustrated by the following Examples.

EXAMPLE 1

101 g (0.167 mole) of a 25% sodium bromate solution is added dropwise, in the course of 30 minutes, to a mixture, cooled to −5° C, of 150 g of ice, 68 g (0.6 mole) of 84% phosphoric acid, 5.8 g (0.1 mole) of sodium chloride and 48.5 g (0.5 mole) of furfurol, with the dropwise addition being regulated to ensure that the temperature does not exceed +1° C. There is added further ice (about 200 g) for cooling the reaction mixture during the addition of the sodium bromate solution. The end point of oxidation is recognisable by a slight yellow colouration of the solution, which increases in intensity as soon as any further drops of bromate solution are added. After completion of the addition of the bromate solution, the reaction mixture is stirred for a further 10 minutes. There is subsequently added to the reaction mixture at −3° C a solution, with a pH value of 1.7, produced by dissolving 146 g (1.5 moles) of sulphamic acid in 140 ml of 30% sodium hydroxide solution and 60 ml of water, whereby there results a pH value of the total mixture of 0.9. The mixture is subsequently stirred firstly for 3 hours at 8° C and then for 30 minutes at 20° C. The resulting 3-hydroxy-2-imino-1(2H)-pyridinesulphonic acid-monohydrate is filtered off, washed three times with 80 ml of water, then with 60 ml of methanol and finally with 60 ml of diethyl ether, and dried in vacuo at room temperature; yield: 62.7 g (60.2% of theory, relative to furfurol).

EXAMPLE 2

101 g (0.167 mole) of a 25% aqueous sodium bromate solution is added dropwise to a mixture, cooled to −5° C, of 68 g (0.6 mole) of 85% phosphoric acid, 160 g of ice, 5.1 g (0.05 mole) of sodium bromide and 48.5 g (0.5 mole) of furfurol, with the addition being made in a manner ensuring that the temperature does not exceed +1° C. The cooling of the reaction mixture is effected by the addition of ice. Into the resulting clear solution there is then introduced a solution, with a pH value of 1.7, obtained by dissolving 146 g (1.5 moles) of sulphamic acid in 140 ml of 30% sodium hydroxide solution and 60 ml of water, whereby a pH value of the whole mixture of 0.9 results. The reaction mixture is subsequently stirred for 2½ hours at 8° C and then for 30 minutes at 20° C. The formed 3-hydroxy-2-imino-1(2H)-pyridinesulphonic acid-monohydrate is filtered off and washed three times with 80 ml of water each time. The content of 3-hydroxy-2-imino-1(2H)-pyridinesulphonic acid-monohydrate in the moist product is determined by dissolving 3 specimens of about 150 mg of the moist product in each case in 50 ml of dimethylformamide/water (4:1) at room temperature, and then titrating with 0.1N sodium hydroxide solution. The content of 3-hydroxy-2-imino-1(2H)-pyridinesulphonic acid-monohydrate is calculated as the mean value of the measured values obtained. THe yield determined in this manner is 58.2% of theory, a value which corresponds to 60.6 g of dry 3-hydroxy-2-imino-1(2H)-pyridinesulphonic acid-monohydrate.

EXAMPLE 3

There is firstly slowly added dropwise a part of 101 g (0.167 mole) of a 25% sodium bromate solution to a mixture, cooled to −5° C, of 150 g of ice, 23 g (0.2 mole) of 85% phosphoric acid, 5.8 g (0.1 mole) of sodium chloride and 48.5 g (0.5 mole) of furfurol, until the pH value has risen to 0.3. The remainder of the sodium bromate solution and 10 ml of 32% hydrochloric acid are then added dropwise within 30 minutes in such a manner that the pH value of the mixture does not exceed 0.3, whereby the addition of ice ensures that the temperature of the reaction mixture does not rise above +1° C. After completion of the addition of the sodium bromate solution, the reaction mixture is stirred for a further 15 minutes, and an addition is subsequently carefully made at −2° C, with good stirring, of about 20 ml of 30% sodium hydroxide solution, until the pH value of the mixture has increased to 0.9. There is subsequently added a solution of 146 g (1.5 mole) of sulphamic acid in 120 ml of 30% sodium hydroxide solution and 60 ml of water. After the addition is completed, the pH value is 1.0 and the temperature is 0° C. Stirring is then maintained for 3 hours at 10° C and for 30 minutes at 20° C; and the formed 3-hydroxy-2-imino-1(2H)-pyridinesulphonic acid-monohydrate is filtered off; it is washed firstly with water, then with methanol and finally with diethyl ether; yield: 58.8 g (54.6% of theory).

If oxidation is performed in the presence of hydrochloric acid, and an addition is subsequently made to the reaction mixture of 146 g (1.5 moles) of sulphamic acid and 185 g (0.486 mole) of trisodium phosphate in 130 ml of water (pH 1.0), there are obtained 56 g (53.8% of theory, relative to furfurol) of 3-hydroxy-2-imino-1(2H)-pyridinesulphonic acid monohydrate.

EXAMPLE 4

101 g (0.167 mole) of a 25% sodium bromate solution is added dropwise to a mixture, cooled to −7° C, of 150 g of ice, 49.2 g (0.6 mole) of phosphorous acid, 5.8 g (0.1 mole) of sodium chloride and 48.5 g (0.5 mole) of furfurol, whereby it is ensured by the addition of ice, that the reaction temperature does not exceed +1° C. After completed addition of the bromate solution, the reaction mixture is stirred for a further 15 minutes, and the pH value of the solution is brought to 0.9 to 1.0 by the addition of about 40 ml of 30% sodium hydroxide solution at −2° C. A solution of 146 g (1.5 moles) of sulphamic acid in 120 ml of 30% sodium hydroxide solution and 60 ml of water (pH 1.0) is then introduced into the reaction mixture, and stirring is maintained for 3 hours at 9° C and for 30 minutes at 20° C. The formed 3-hydroxy-2-imino-1(2H)-pyridinesulphonic acid-monohydrate is filtered off, washed firstly with water, then with methanol and finally with diethyl ether, and dried in vacuo; yield 57.9 g (55.6% of theory relative to furfurol).

With the use of 0.3 mole of phosphorous acid per mole of furfurol instead of 0.6 mole, the procedure being otherwise the same, there is obtained 57.3 g (55.0% of theory, relative to furfurol) of 3-hydroxy-2-imino-1(2H)-pyridinesulphonic acid-monohydrate.

EXAMPLE 5

101 g (0.167 mole) of a 25% sodium bromate solution is added dropwise to a mixture, cooled to −4° C, of 500 g of ice, 70 g (0.4 mole) of pyrophosphoric acid, 5 g (0.086 mole) of sodium chloride and 48.5 g (0.5 mole) of furfurol, whereby the addition is so regulated that the temperature does not exceed +1° C. After completed addition of the bromate solution, stirring is maintained for a further 10 minutes. The pH value of the reaction mixture is subsequently adjusted to 1 by the careful addition of 30% sodium hydroxide solution, and a solution of 146 g (1.5 moles) of sulphamic acid in 140 ml of 30% sodium hydroxide solution and 60 ml of water is added. The mixture is afterwards stirred firstly for 3 hours at 8° C and then for 30 minutes at 20° C. The precipitated monohydrate of 3-hydroxy-2-imino-1(2H)-pyridinesulphonic acid is filtered off, washed three times with 80 ml of water each time, then with 60 ml of methanol and finally with 60 ml of diethyl ether, and dried in vacuo at room temperature; yield: 56.6 g (54.4% of theory, relative to furfurol).

EXAMPLE 6

50.5 g (0.0835 mole) of a 25% sodium bromate solution is added dropwise to a mixture, cooled to −5° C, of 250 g of ice, 29 g (0.3 mole) of methanephosphonic acid, 5 g (0.086 mole) of sodium chloride and 24.3 g (0.25 mole) of furfurol, with the dropwise addition being regulated to ensure that the temperature does not exceed +1° C. After completed addition of the bromate solution, the reaction mixture is stirred for 10 minutes. The pH value of the mixture is subsequently brought to 1 by careful addition of 30% sodium hydroxide solution; and a solution of 73 g (0.75 mole) of sulphamic acid in 70 ml of 30% sodium hydroxide solution and 30 ml of water is added. The resulting reaction mixture is stirred firstly for 3 hours at 8° C and then for 30 minutes at 20° C. The precipitated monohydrate of 3-hydroxy-2-imino-1(2H)-pyridinesulphonic acid is afterwards filtered off, washed firstly with water, then with methanol and finally with diethyl ether, and dried in vacuo at room temperature; yield: 30 g (57.6% of theory, relative to furfurol).

EXAMPLE 7

80 g (0.5 mole) of bromine is added dropwise at −4° to −2° C, in the course of 30 minutes, to a mixture of 500 g of ice, 68 g (0.6 mole) of 85% phosphoric acid, 5.8 g (0.1 mole) of sodium chloride and 48.5 g (0.5 mole) of furfural, the pH value of which has been adjusted to 0.2 by the addition of sodium hydroxide solution. By the simultaneous addition of sodium hydroxide solution, the pH value of the reaction mixture is kept always at 0.2. After completed addition of the bromine, the pH value of the reaction mixture is brought to 1.0 by careful addition of sodium hydroxide solution. To the solution obtained in this manner there is added at −2° to 0° C a solution of 146 g (1.5 moles) of sulphamic acid in 140 ml of 30% sodium hydroxide solution and 60 ml of water. Stirring is subsequently maintained for 2½ hours at 7° to 11° C and then for a further 30 minutes at 20° C. There is obtained 56 g (53.8% of theory, relative to furfurol) of 3-hydroxy-2-imino-1(2H)-pyridinesulphonic acid-monohydrate.

EXAMPLE 8

115 ml (0.25 mole) of a 13% sodium hypochlorite solution is added dropwise during 40 minutes, with slight external cooling, to a mixture of 350 g of ice water, 60 ml (0.9 mole) of phosphoric acid and 24.3 g (0.25 mole) of furfural, the manner of addition being such that the temperature does not exceed −2° C. After completed addition of the sodium hypochlorite solution, the pH value of the colourless solution is adjusted to 1.0 by careful addition of 30% sodium hydroxide solution. To the solution thus obtained there is subsequently added at −2° to 0° C a solution of 73 g (0.75 mole) of sulphamic acid in 70 ml of 30% sodium hydroxide solution and 30 ml of water; stirring is maintained firstly for 2½ hours at 7° to 9° C and then for a further 30 minutes at 20° C, and the reaction mixture is afterwards filtered. The resulting monohydrate of 3-hydroxy-2-imino-1(2H)-pyridinesulphonic acid is washed on the filter firstly with water, then with methanol and finally with diethyl ether; yield: 24.7 g (47.5% of theory, relative to furfurol).

EXAMPLE 9

37 g (0.52 mole) of chlorine is introduced at −5° to −3° C during 30 minutes into a mixture of 400 ml of ice water, 40 ml (0.6 mole) of 85% phosphoric acid, 20.4 g (0.2 mole) of sodium bromide and 48.5 g (0.5 mole) of furfurol, whereby there occurs intermediately a slight resinous precipitation which disappears towards the end of oxidation. After completed chlorine addition, stirring is maintained for 5 minutes. The pH value of the solution is then adjusted to 1.0 by the careful addition of 133 ml of 30% sodium hydroxide solution. To the solution thus obtained there is subsequently added a solution of 146 g (1.5 moles) of sulphamic acid in 140 ml of 30% sodium hydroxide solution and 60 ml of water. The reaction mixture is afterwards stirred firstly for 2½ hours at 8° C and then for a further 30 minutes at 20° C, and thereupon filtered. The resulting monohydrate of 3-hydroxy-2-imino-1(2H)-pyridinesulphonic acid is washed on the filter firstly with water, then with methanol and finally with diethyl ether, and dried in vacuo; yield: 50.1 g (48.1% of theory, relative to furfurol).

I claim:

1. Process for the production of 3-hydroxy-2-imino-1(2H)-pyridinesulphonic acid monohydrate by oxidation of furfurol and reaction of the oxidation product with sulphamic acid, which process comprises oxidising furfurol in an aqueous medium at a temperature of −10° C to 0° C, with a pH value of 0 to 0.5, in the presence of an oxyacid of tri- or pentavalent phosphorus or of a water-soluble salt of such an acid and with the oxidising agent being chlorine, alkali hypochlorite, bromine, sodium bromate, potassium bromate or chlorine in the presence of hydrogen bromide; subsequently reacting the oxidation product with 2 to 3 moles of sulphamic acid per mole of employed furfurol; and then separating the formed 3-hydroxy-2-imino-1(2H)-pyridinesulphonic acid monohydrate.

2. Process according to claim 1, wherein the employed oxyacid of tri- or pentavalent phosphorus is phosphoric acid, pyrophosphoric acid, metaphosphoric acid, phosphorous acid or a water-soluble phosphonic acid, or a water-soluble salt of one of these acids.

3. Process according to claim 1, wherein the employed oxyacid of tri- or pentavalent phosphorus is phosphoric acid or phosphorous acid, or a water-soluble salt of one of these acids.

4. Process according to claim 1, wherein there is used an oxyacid of tri- or pentavalent phosphorus in an amount of 0.4 to 4 moles per mole of employed furfurol.

5. Process according to claim 1, wherein there is used an oxyacid of tri- or pentavalent phosphorus in an amount of about 1 mole per mole of employed furfurol.

6. Process according to claim 1, wherein the oxidising agent used is sodium bromate or potassium bromate.

7. process according to claim 1, wherein oxidation is performed in the presence of 0.01 to 1 mole of an alkali chloride or alkaline-earth chloride or of an alkali bromide or alkaline-earth bromide.

8. Process according to claim 1, which process comprises the oxidation of furfurol in an aqueous medium with the stoichiometric amount of sodium bromate or potassium bromate at −8° to −2° C, with a pH value of 0 to 0.3, in the presence of 1 mole of phosphoric acid or phosphorous acid and 0.1 to 0.3 mole of an alkali chloride or alkaline-earth chloride or of an alkali bromide or alkaline-earth bromide; the addition to the reaction mixture immediately afterwards, at −5° to 0° C, of a solution, adjusted to pH 1 or 2, of 3 moles of sulphamic acid per mole of employed furfurol; and the complete reaction of the mixture at 5° to 25° C.

* * * * *